United States Patent [19]

Gauthier-Lafaye et al.

[11] Patent Number: 4,609,504
[45] Date of Patent: Sep. 2, 1986

[54] PROCESS FOR THE PREPARATION OF ACETIC ANHYDRIDE

[75] Inventors: Jean Gauthier-Lafaye, Lyons; Robert Perron, Charly, both of France

[73] Assignee: Rhone-Poulenc Industries, Paris, France

[21] Appl. No.: 331,828

[22] Filed: Dec. 17, 1981

[30] Foreign Application Priority Data

Dec. 24, 1980 [FR] France ............... 80 27941

[51] Int. Cl.$^4$ ............................................. C07C 51/56
[52] U.S. Cl. ................................................... 260/549
[58] Field of Search ......................................... 260/549

[56] References Cited

U.S. PATENT DOCUMENTS

| | | | |
|---|---|---|---|
| 2,789,137 | 4/1957 | Reppe et al. | 260/549 |
| 4,002,677 | 1/1977 | Naglieri et al. | 260/549 |
| 4,002,678 | 1/1977 | Naglieri et al. | 260/549 |
| 4,134,912 | 1/1979 | Naglieri et al. | 562/579 |
| 4,239,698 | 12/1980 | Isshiki et al. | 260/549 |
| 4,351,953 | 9/1982 | Gauthier-Lafaye | 562/519 |

OTHER PUBLICATIONS

*Hackh's Chemical Dictionary*, 4th Ed. (1969) McGraw-Hill, Publ., at p. 26.
Onouchi, Takeshi et al., *Chemical Abstracts*, vol. 80 (1974), #107,994f.
Gauthier-Lafaye, Jean et al., *Chemical Abstracts*, vol. 94 (1981), #156,327p. (Eur. Pat. Appln. No. 18,927 dtd. Nov. 12, 1980).
Falbe, Jurgen, "Carbon Monoxide In Organic Synthesis" (1970), p. 113, Springer, Publ.

*Primary Examiner*—Natalie Trousof
*Assistant Examiner*—L. Hendriksen
*Attorney, Agent, or Firm*—Burns, Doane, Swecker & Mathis

[57] ABSTRACT

The invention relates to a process for the preparation of acetic anhydride by carbonylation. In the process, carbon monoxide is reacted with methyl acetate in an anhydrous medium, in the liquid phase, in the presence of an effective amount of nickel, methyl iodide, a quaternary ammonium or quaternary phosphonium iodide and a lithium salt, the reaction medium initially containing acetic anhydride, if desired.

20 Claims, No Drawings

PROCESS FOR THE PREPARATION OF ACETIC ANHYDRIDE

CROSS-REFERENCE TO RELATED APPLICATION

Gauthier-Lafaye et al copending application, Ser. No. 331,809, filed concurrently herewith, assigned to the assignee hereof, and expressly incorporated by reference herein.

BACKGROUND OF THE INVENTION

1. Field of the Invention

The present invention relates to a process for the preparation of acetic anhydride by the carbonylation of methyl acetate.

2. Description of the Prior Art

It is well known that acetic anhydride can be produced by the carbonylation of methyl acetate under relatively severe pressure conditions, in the presence of nickel complexes of the formula $$[A_4M]_2NiX_4$$

in which X represents a bromine or iodine atom, M represents a phosphorus or nitrogen atom and A is, for example, a lower alkyl radical; compare U.S. Pat. No. 2,729,651. These complexes, which are obtained by reacting nickel halides with quaternary phosphonium or ammonium halides, can be used in this form in the reaction in question, or alternatively they can be formed in situ. However, the efficiency of this type of process is low, despite the high pressures used.

More recent work (compare British Patent Application No. 2,007,666) has shown that substantially milder conditions can be used during the carbonylation of methyl acetate in the presence of nickel, iodine (or an iodine compound) and a promoter chosen from among organic compounds of the trivalent elements of the nitrogen group; considerable amounts of acetic anhydride can then be obtained provided that the following two conditions are satisfied simultaneously:

the iodine (or the iodine compound) must be used in a proportion such that the fraction of iodine which is not chemically bonded either to the nickel or to the promoter is at least 0.2 mol (of elementary iodine) per mol of both the nickel compound and the promoter; and the reaction in question must be carried out in an aliphatic carboxylic acid as the solvent.

From an examination of the techniques proposed earlier, it is apparent that it would be desirable to be able to produce acetic anhydride efficiently by the carbonylation of methyl acetate, in the presence of a nickel-based catalyst system, without using organic solvents foreign to the reaction medium, while at the same time carrying out the reaction under relatively mild pressure conditions. It would also be very desirable to improve the productivity of the nickel-based catalyst system.

SUMMARY OF THE INVENTION

It has now been found that it is possible to prepare acetic anhydride efficiently by the carbonylation of methyl acetate in the presence of a nickel-based catalyst system, in the absence of solvents foreign to the reaction medium, said medium containing only the starting material, the catalyst system and, if appropriate, greater or lesser amounts of the reaction product.

The present invention thus relates to a process for the preparation of acetic anhydride by the carbonylation of methyl acetate in an anhydrous medium, in the liquid phase, in the presence of an effective amount of nickel, methyl iodide, a quaternary ammonium or quaternary phosphonium iodide and a lithium salt, the reaction medium initially containing acetic anhydride, if desired.

The process according to the invention requires the presence of an effective amount of nickel. Any source of nickel can be used within the scope of the present process. The nickel can be introduced in the form of the metal itself (for example, RANEY nickel) or in any other convenient form. The following may be mentioned as examples of nickel compounds which can be used to carry out the present process: nickel carbonate, oxide, hydroxide, halides, in particular iodide, and carboxylates, in particular acetate.

Nevertheless, if a nickel salt is introduced, it is possible to observe a longer or shorter induction period and it may therefore be preferable to use compounds of nickel zero, such as nickel tetracarbonyl and bis-(triphenylphosphine)-nickel dicarbonyl. Of course, those skilled in the art will be able to determine the appropriate forms of the nickel compounds and they will naturally see that the precise form in which the nickel is introduced into the reaction medium is not of fundamental importance, especially in the context of a continuous process.

The precise amount of nickel is not critical, just so long as an effective amount is employed. The proportion of nickel, which influences the reaction rate, is determined as a function of that reaction rate which is considered to be suitable, taking into account the other reaction parameters. Generally speaking, an amount of between 5 and 2,000 milligram atoms of nickel per liter of solution leads to satisfactory results. The reaction is preferably carried out with a proportion of between 20 and 1,000 milligram atoms of nickel per liter.

In order to carry out the present invention, the presence of methyl iodide in the reaction medium is also required. It is not necessary for this component of the catalyst system to be introduced initially and it is possible, for example, to use free iodine, hydriodic acid, an alkyl iodide which is different from methyl iodide, or an acyl iodide. As is known to those skilled in the art, iodine and these types of iodine compounds can be considered as precursors of methyl iodide in the reaction in question.

In general, methyl iodide is present in the reaction medium in an amount of 1 to 100 mols and preferably in an amount of 5 to 50 mols per gram atom of nickel present in the medium.

The catalyst system used within the scope of the present process also comprises a quaternary ammonium or quaternary phosphonium iodide.

The precise nature of these iodides is not of fundamental importance and the choice from among these compounds is governed chiefly by considerations of a practical nature, such as availability, convenience of use and solubility in the reaction medium, which medium is free of foreign organic solvent, as has already been specified. In this respect, use of quaternary ammonium or phosphonium iodides whose cations are represented respectively by the formulas (I) and (II)

$$R_1N^+(R_2)_3 \qquad (I)$$

$$R_1P^+(R_2)_3 \qquad (II)$$

in which $R_1$ and $R_2$, which can be identical or different, represent linear alkyl radicals having at most 4 carbon atoms, it also being possible for $R_2$ to represent a phenyl, tolyl or xylyl radical, is recommended.

Examples which may be mentioned of quaternary ammonium iodides suitable for carrying out the present process are tetramethylammonium, triethylmethylammonium, tributylmethylammonium, tributyl-(n-propyl)-ammonium, tetraethylammonium and tetrabutylammonium iodides.

Examples which may be mentioned of quaternary phosphonium iodides suitable for carrying out the present process are methyltriphenylphosphonium, ethyltriphenylphosphonium, methyltrixylylphosphonium and methyltributylphosphonium iodides.

Of course, this type of compound, which must be present in order to carry out the present invention, can be formed in situ from the corresponding amine or phosphine introduced, if appropriate, in the form of a nickel complex such as bis-(triphenylphosphine)-nickel dicarbonyl, and from an alkyl iodide. If this procedure is chosen, it will be appropriate to introduce, in addition to the amine (or phosphine) in question, the amount of alkyl iodide (if appropriate, methyl iodide) required for its quaternization, so that this conversion in situ does not take place to the detriment of the methyl iodide, which must also be present in the reaction medium.

Mixtures of such compounds can also be used. In general, these compounds are present in the reaction medium in an amount such that the atomic ratio of the phosphorus and/or the nitrogen to the nickel is between 0.2 and 50 and preferably between 0.2 and 20. Advantageously, this ratio is between 0.5 and 10. Quaternary phosphonium iodides are particularly suitable for use in carrying out the present process.

In the process forming the subject of the present invention, it is essential for the catalyst system to contain a lithium salt. The precise nature of the anion of this salt is not of fundamental importance and the following may be mentioned as examples of lithium salts which can be used within the scope of the present process: lithium hydroxide, chloride, bromide, iodide, carbonate and nitrate, and also lithium carboxylates containing at most 12 carbon atoms.

Among these salts, lithium iodide, carbonate and carboxylates are particularly suitable for carrying out the present invention. A lithium carboxylate having at most 5 carbon atoms is preferably used, lithium acetate proving particularly effective.

In general, a lithium salt (or several lithium salts) is (or are) used in an amount such that the atomic ratio of the lithium to the nickel is between 1 and 100, although smaller or larger amounts can be used. Good results are obtained for an atomic ratio Li/Ni of between 2 and 25.

The catalyst system defined above proves particularly effective for preparing acetic anhydride by the carbonylation of methyl acetate in the liquid phase, without using solvents foreign to the reaction medium.

It has also been found, totally unexpectedly, that not only does the acetic anhydride (reaction product) not inhibit the carbonylation reaction in the presence of the catalyst system in question, but it tends to favor the correct course of this reaction.

Thus, according to an advantageous embodiment of the present process, the reaction is carried out on a mixture of methyl acetate and acetic anhydride in which the acetic anhydride represents on the order of 10 to 90% by volume and preferably on the order of 20 to 80% of the volume.

When the reaction is carried out in a batchwise process, there is every advantage in introducing the desired amount of acetic anhydride from the start, and when the reaction is carried out continuously, it is appropriate to adjust the flow rate of the various materials at the inlet and the outlet of the reaction zone, so that the desired amount of acetic anhydride is present in the reaction zone. In the latter case, it can prove useful to recycle part of the acetic anhydride produced into the reaction zone.

As indicated hereinabove, the reaction is carried out in the liquid phase, under a pressure above atmospheric pressure. In general, it is carried out under a total pressure of more than 15 bars; it serves no purpose, however, to reach 700 bars. To carry out the invention satisfactorily, a total pressure of 25 to 200 bars is recommended.

The reaction temperature is generally above 140° C., but it is not necessary to reach 300° C. Good results are obtained within the temperature range from 160° to 220° C.

Carbon monoxide is preferably used in the essentially pure form, as available commercially. However, the presence of impurities, such as carbon dioxide, oxygen, methane and nitrogen, can be tolerated. The presence of hydrogen is not detrimental, even in relatively large proportions.

At the end of the operation, the acetic anhydride obtained is separated from the other constituents of the reaction medium by any suitable method, for example by distillation.

In order to further illustrate the present invention and the advantages thereof, the following specific examples are given, it being understood that same are intended only as illustrative and in nowise limitative. In the examples which follow, RY (%) denotes the number of mols of acetic anhydride produced per 100 mols of methyl acetate introduced, and Pr denotes the productivity in grams of acetic anhydride per hour and per liter of the initial reaction medium.

EXAMPLE 1

The following were introduced into a Hastelloy B2 autoclave having a capacity of 125 ml:
 25 ml of methyl acetate
 20 ml of acetic anhydride
 89 millimols of methyl iodide
 4 mg atoms of nickel in the form of bis-(triphenylphosphine)-nickel dicarbonyl
 12 millimols of methyltriphenylphosphonium iodide and
 100 millimols of lithium acetate.

After closing the autoclave, a pressure of 40 bars of carbon monoxide was established. Shaking by means of a reciprocating system was started and the autoclave was heated to 180° C., over the course of about 25 minutes, by means of an annular furnace. The pressure in the autoclave was kept constant and equal to 70 bars by continuously supplying carbon monoxide. After a reaction time of 2 hours at the temperature indicated, the results obtained were as follows:
 RY (%)=60
 Pr=190.
 Control experiment (a):
 Example 1 above was repeated in the absence of lithium acetate. The results obtained were as follows:

RY (%)=15
Pr=48.

A comparison of these results with those obtained in Example 1 shows that the presence of a lithium salt makes it possible to increase the amount of acetic anhydride by a factor on the order of 4.

EXAMPLE 2

Using an autoclave and the procedure described above, an experiment was carried out on a charge consisting of:
- 25 ml of methyl acetate
- 20 ml of acetic anhydride
- 90 millimols of methyl iodide
- 4 mg atoms of nickel in the form of bis-(triphenylphosphine)-nickel dicarbonyl
- 12 millimols of methyltriphenylphosphonium iodide and
- 50 millimols of lithium carbonate.

The results obtained after a reaction time of 2 hours at 180° C. and under a total pressure of 90 bars were as follows:
RY (%)=56
Pr=175.

EXAMPLE 3

Example 2 above was repeated, the lithium carbonate being replaced by 40 millimols of lithium iodide, and only 79 millimols of methyl iodide being introduced. The results were as follows:
RY (%)=46
Pr=145.

EXAMPLE 4

Using an autoclave and the procedure described above, an experiment was carried out on a charge consisting of:
- 25 ml of methyl acetate
- 20 ml of acetic anhydride
- 96 millimols of methyl iodide
- 4 mg atoms of nickel in the form of bis-(triphenylphosphine)-nickel dicarbonyl
- 12 millimols of methyltriphenylphosphonium iodide and
- 40 millimols of lithium acetate.

The results obtained after a reaction time of 2 hours at 180° C. under a total pressure of 70 bars, including 20 bars of hydrogen partial pressure, were as follows:
RY (%)=45
Pr=145.

EXAMPLE 5

Using an autoclave and the procedure described above, an experiment was carried out on a charge consisting of:
- 25 ml of methyl acetate
- 20 ml of acetic anhydride
- 80 millimols of methyl iodide
- 4 mg atoms of nickel in the form of nickel tetracarbonyl
- 20 millimols of methyltriphenylphosphonium iodide and
- 40 millimols of lithium acetate.

The results obtained after a reaction time of 2 hours at 180° C. and under a total pressure of 90 bars were as follows:
RY (%)=63
Pr=200.

EXAMPLE 6

Example 5 above was repeated, the amount of methyltriphenylphosphonium iodide being reduced by a factor of 5. The results were as follows:
RY (%)=66
Pr=210.

Control experiment (b):

Example 5 above was repeated in the absence of methyltriphenylphosphonium iodide, the reaction time being only 1 hour 30 minutes. The results obtained were as follows:
RY (%)=6
Pr=25.

EXAMPLES 7 TO 13

Using the autoclave and the procedure described for Example 1, a series of experiments were carried out on a charge consisting of: 25 ml of methyl acetate, 20 ml of acetic anhydride, 40 millimols of lithium acetate, methyl iodide, bis-(triphenylphosphine)-nickel dicarbonyl and, if appropriate, methyltriphenylphosphonium iodide. The particular conditions and also the results obtained after a reaction time of 2 hours at 180° C. are summarized in the table below, in which $P_T$ denotes the total pressure and $P^+I^-$ (millimols) denotes the amount of methyltriphenylphosphonium iodide introduced.

TABLE

| No. | Nickel (mg atoms) | $CH_3I$ (millimols) | $P^+I^-$ (millimols) | $P_T$ (bars) | RY (%) | Pr |
|---|---|---|---|---|---|---|
| 7 | 4 | 35 | 12 | 70 | 36 | 115 |
| 8 | 2 | 85 | 16 | 90 | 40.5 | 125 |
| 9 | 4 | 88 | 12 | 70 | 54 | 170 |
| 10 | 8 | 95 | 4 | 70 | 59 | 190 |
| 11 | 4 | 160 | 12 | 70 | 62 | 195 |
| 12 | 4 | 89 | 11 | 90 | 65 | 210 |
| 13 | 4 | 88 | 0 | 90 | 71 | 225 |

EXAMPLE 14

Using the autoclave and the procedure described for Example 1, an experiment was carried out on a charge consisting of:
- 45 ml of methyl acetate
- 80 millimols of methyl iodide
- 4 mg atoms of nickel in the form of bis-(triphenylphosphine)-nickel dicarbonyl
- 12 millimols of methyltriphenylphosphonium iodide and
- 19.8 millimols of lithium acetate.

The results obtained after a reaction time of 2 hours at 180° C. and under a total pressure of 70 bars were as follows:
RY (%)=19
Pr=110.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What we claim is:

1. A process for the preparation of acetic anhydride which comprises carbonylating methyl acetate in an anhydrous medium, in the liquid phase, in the presence of an effective amount of a catalyst comprised of nickel, methyl iodide, a quaternary ammonium or quaternary phosphonium iodide and a lithium salt, at a total pressure between about 25 and 200 bars, said anhydrous medium consisting of components selected from the group consisting of (1) methyl acetate and said catalyst and (2) methyl acetate, said catalyst and acetic anhydride.

2. A process according to claim 1, wherein the reaction mixture initially contains a solvent quantity of acetic anhydride.

3. A process according to claim 1 or 2, wherein the temperature is between about 140° and 300° C.

4. A process according to claim 1 or 2, wherein the temperature is between about 160° and 220° C.

5. A process according to claim 1 or 2, wherein the concentration of nickel is between about 5 and about 200 milligram atoms per liter of reaction medium.

6. A process according to claim 1 or 2, wherein the concentration of nickel is between about 20 and about 100 milligram atoms per liter of reaction medium.

7. A process according to claim 1 or 2, wherein the methyl iodide is present in the reaction medium in an amount of from about 1 to about 100 mols per gram atom of nickel.

8. A method according to claim 1 or 2, wherein the methyl iodide is present in the reaction medium in an amount of from about 5 to about 50 mols per gram atom of nickel.

9. A process according to claim 1 or 2, wherein the reaction is carried out in the presence of a quaternary phosphonium iodide.

10. A process according to claim 1 or 2, wherein the atomic ratio of the phosphorus and/or the nitrogen to the nickel is between about 0.2 and about 50.

11. A process according to claim 1 or 2, wherein the atomic ratio of the phosphorus and/or the nitrogen to the nickel is between about 0.2 and about 20.

12. A process according to claim 1 or 2, wherein the lithium salt is lithium iodide.

13. A process according to claim 1 or 2, wherein the lithium salt is lithium carbonate.

14. A process according to claim 1 or 2, wherein the lithium salt is a lithium carboxylate having at most 12 carbon atoms.

15. A process according to claim 1 or 2, wherein the lithium salt is a lithium carboxylate having at most 5 carbon atoms.

16. A process according to claim 1 or 2, wherein the lithium salt is lithium acetate.

17. A process according to claim 1 or 2, wherein the atomic ratio of the lithium to the nickel is between about 1 and about 100.

18. A process according to claim 1 or 2, wherein the atomic ratio of the lithium to the nickel is between about 2 and about 25.

19. A process according to claim 2, wherein the reaction is carried out on a mixture of methyl acetate and acetic anhydride, the acetic anhydride representing from about 10 to about 90% of the volume of said mixture of methyl acetate and acetic anhydride.

20. A process according to claim 2, wherein the reaction is carried out on a mixture of methyl acetate and acetic anhydride, the acetic anhydride representing from about 20 to about 80% of the volume of said mixture of methyl acetate and acetic anhydride.

* * * * *